Figure 2:
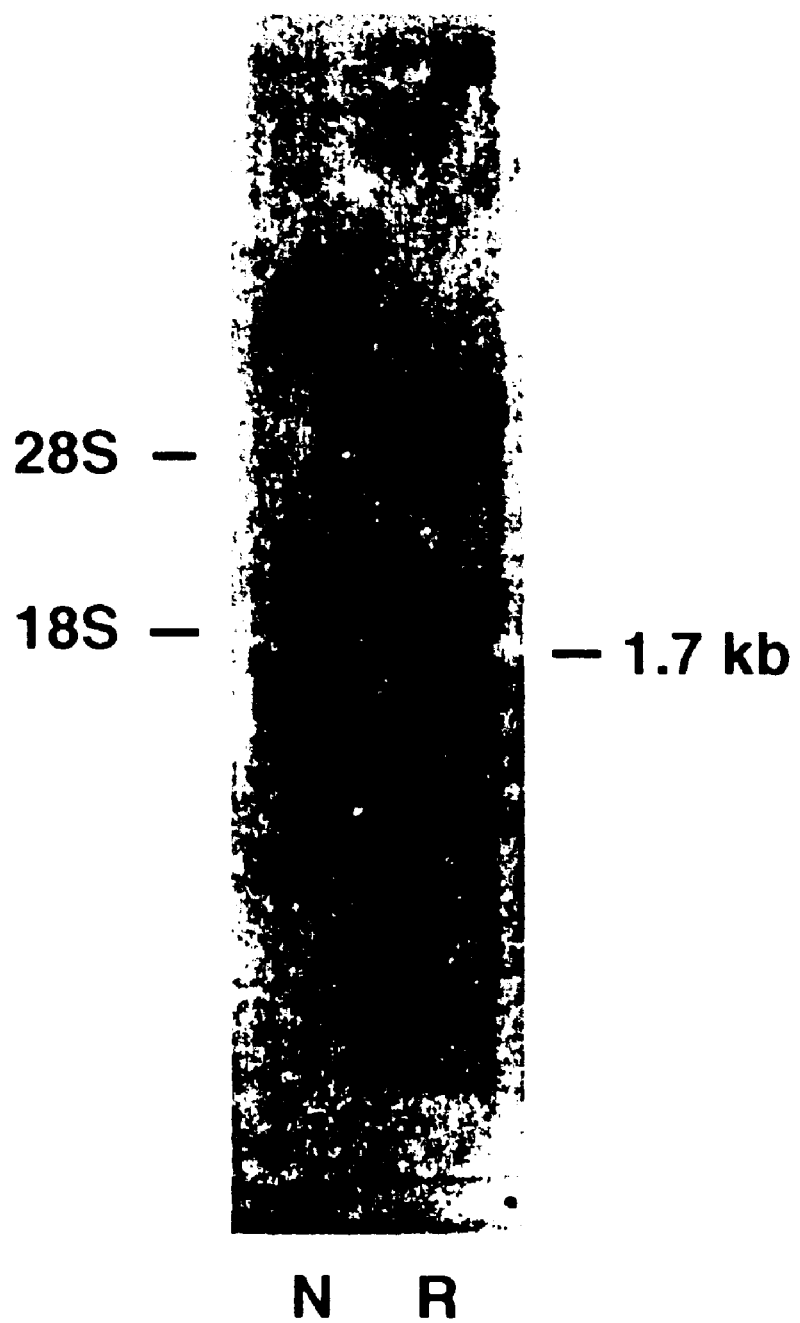

United States Patent [19]
Purchio et al.

[11] Patent Number: 6,027,935
[45] Date of Patent: Feb. 22, 2000

[54] GENE UP-REGULATED IN REGENERATING LIVER

[75] Inventors: Anthony F. Purchio, Solana Beach; Liguo New, San Diego; Kang Liu, San Diego; Vafa Kamali, San Diego; Brian Naughton, El Cajon, all of Calif.

[73] Assignee: Advanced Tissue Sciences, Inc., La Jolla, Calif.

[21] Appl. No.: 08/660,347

[22] Filed: Jun. 5, 1996

Related U.S. Application Data

[63] Continuation-in-part of application No. 08/471,038, Jun. 6, 1995, abandoned.
[51] Int. Cl.$^7$ .............................. C12N 5/00; C12N 15/00; C12N 15/63
[52] U.S. Cl. ...................... 435/325; 435/69.1; 435/320.1; 435/91.2; 435/455; 536/23.5; 536/24.31; 424/93.21; 514/44
[58] Field of Search .............................. 514/44; 435/69.1, 435/172.3, 91.2, 320.1, 325, 455; 424/93.21; 935/23; 536/23.5, 24.31

[56] References Cited

U.S. PATENT DOCUMENTS

| | | | |
|---|---|---|---|
| 5,266,480 | 11/1993 | Naughton et al. | 435/240 |
| 5,585,479 | 12/1996 | Hoke et al. | 536/24.5 |

OTHER PUBLICATIONS

Orkin et al., Report and Recommendations of the Panel to Assess the NIH Investment in Research on Gene Therapy, Dec. 7, 1995.
Eck & Wilson, "Gene–Based Therapy", Goodman & Gilman's The Pharmacological Basis of Therapeutics, Ninth Edition, Chapter 5, pp. 77–101, 1995.
Gura, Science, vol. 270, pp. 575–577, Oct. 27, 1995.
Bao et al., 1988, "Molecular structure and sequence homology of a gene related to $\alpha_1$–antitrypsin in the human genome", Genomics 2:165–173.
Berry & Friend, 1969, "High–yield preparation of isolated rat liver parenchymal cells", J. Cell. Biol. 43:506–520.
Bollen et al., 1983, "Cloning and expression in Escherichia coli of full–length complementary DNA coding for human $\alpha_1$–antitrypsin", DNA 2:255–264.
Carrell & Boswell, 1986, "Serpins: The superfamily of plasma serine proteinase inhibitors in proteinase inhibitors", Barrett & Salvensen, eds. Elsevier, Amsterdam, pp. 403–420.
Carrell & Travis, 1985, "$\alpha_1$–antitrypsin and the serpins: variation and countervariation", Trends in Biochem. Sci. 10:20–24.
Chandra et al., 1983, "Sequence homology between human $\alpha_1$–antichymotrypsin, $\alpha_1$–antitrypsin, and antithrombin III", Biochem. 22:5055–5061.
Flink et al., 1986, "Complete amino acid sequence of human thyroxine–binding globulin deduced from cloned DNA: Close homology to the serine", Proc. Natl. Acad. Sci. USA 83:7708–7712.

Guguen–Guillouzo et al., 1982, "High yield preparation of isolated human adult hepatocytes by enzymatic perfusion of the liver", Cell Biol. Int. Rep. 6:625–628.
Guillouzo & Guguen–Guillouzo, eds., 1986, "Isolated & Culture Hepatocytes", Paris, INSERM, and London, J. Libbey Eurotext, pp. 1–12.
Hagiya et al., 1994, "Cloning and sequence analysis of the rat augmenter of liver regeneration (ALR) gene: Expression of biologically active recombinant ALR and demonstration of tissue distribution", Proc. Natl. Acad. Sci. USA 9:8142–8146.
Hammond et al., 1991, "Molecular studies of corticosteroid binding globulin structure, biosynthesis and function", J. Steroid Biochem. Mol. Biol. 40:755–762.
Herzog et al., 1991, "Complete nucleotide sequence of the gene for human heparin cofactor II and mapping to chromosomal band 22q11", Biochem. 30:1350–1357.
Holland et al., 1992, "A major estrogen–regulated protein secreted from the liver of Xenopus laevis is a memeber of the serpin superfamily", J. Biol. Chem. 267:7053–7059.
Hsu et al., 1992, "Interactions among LRF–1, JunB, c–Jun, and c–Fos define a regulatory program in the $G_1$ phase of liver regeneration", Mol. Cell Biol. 12:4654–4665.
Mohn et al., 1991, "The immediate–early growth response in regenerating liver and insulin–stimulater H–35 cells" Comparison with serum–stimulated 3T3 cells and identification of 41 novel immediate–early genes, Mol. Cell Biol. 11:381–390.
Morii & Travis, 1983, "Amino acid sequence at the reactive site of human $\alpha_1$–antichumotrypsin", J. Biol. Chem. 258:12749–12752.
Naughton et al., 1977, "Hepatic regeneration and erythropoietin production in the rat", Science 196:301–302.
Owen et al., 1983, "Mutation of antitrypsin to antithrombin", New Engl. J. Med. 309:694–698.
Pages et al., 1990, "Molecular characterization of three rat liver serine–protease inhibitors affected by inflammation and hypophysectomy", Eur. J. Biochem. 190:385–391.
Suzuki et al., 1987, "Characterization of a cDNA for human protein C inhibitor", J. Biol. Chem. 262:611–616.

Primary Examiner—Brian R. Stanton
Assistant Examiner—Jill D. Martin
Attorney, Agent, or Firm—Pennie & Edmonds LLP

[57] ABSTRACT

The novel gene, Rasp-1, which is up-regulated in regenerating liver, is disclosed. The novel RASP-1 protein, which is encoded by the Rasp-1 gene, is also disclosed. In addition, antibodies against the Rasp-1 gene products are also disclosed. Furthermore, the use of Rasp-1 nucleic acid sequences, Rasp-1 gene products, and antibodies against Rasp-1 gene products in the treatment and diagnosis of liver disorders is also disclosed.

11 Claims, 10 Drawing Sheets

|    | 1 | 2 | 3 | 4 | 5 | 6 | 7 | 8 | 9 | 10 | 11 |    |
|----|---|---|---|---|---|---|---|---|---|----|----|----|
|    |   | 1 | 2 | 3 | 4 | 5 | 6 | 7 | 8 | 9  | 10 | 11 | RASP1 |
| 1  |   | 31.5 | 30.5 | 29.2 | 29.3 | 29.5 | 29.2 | 27.7 | 27.9 | 27.3 | 26.5 | 1 | A1AT hu |
| 2  | 66.1 |   | 24.9 | 45.2 | 44.8 | 43.4 | 59.8 | 37.6 | 41.9 | 42.2 | 43.9 | 2 | HEP2 hu |
| 3  | 66.7 | 70.4 |   | 24.5 | 25.7 | 25.7 | 22.0 | 26.5 | 26.4 | 23.7 | 27.6 | 3 | IPSP hu |
| 4  | 66.8 | 52.2 | 69.6 |   | 47.5 | 42.9 | 38.8 | 35.6 | 47.2 | 38.5 | 42.0 | 4 | AACT hu |
| 5  | 67.4 | 52.9 | 68.5 | 49.3 |   | 56.6 | 39.0 | 35.9 | 62.5 | 42.7 | 44.5 | 5 | SPI1 rat |
| 6  | 67.2 | 54.1 | 68.5 | 53.5 | 41.9 |   | 40.2 | 36.2 | 70.8 | 40.2 | 41.9 | 6 | A1AU hu |
| 7  | 67.9 | 40.2 | 74.0 | 59.3 | 58.7 | 57.6 |   | 31.2 | 37.6 | 35.8 | 38.1 | 7 | EP45 xen |
| 8  | 67.1 | 60.6 | 69.7 | 60.5 | 61.0 | 60.7 | 67.2 |   | 35.6 | 36.4 | 35.6 | 8 | SPI3 rat |
| 9  | 68.6 | 55.4 | 66.8 | 50.1 | 36.7 | 28.3 | 59.8 | 61.1 |   | 42.4 | 42.4 | 9 | THBG hu |
| 10 | 68.8 | 56.4 | 71.6 | 59.1 | 55.1 | 56.7 | 62.2 | 61.0 | 54.8 |   | 41.0 | 10 | CBG hu |
| 11 | 71.2 | 55.6 | 68.7 | 55.9 | 52.9 | 56.3 | 61.5 | 61.7 | 55.0 | 57.7 |    | 11 |  |
|    | 1 | 2 | 3 | 4 | 5 | 6 | 7 | 8 | 9 | 10 | 11 |    |

Percent Similarity (upper triangle) / Percent Divergence (lower triangle)

FIG. 3E

GENE UP-REGULATED IN REGENERATING LIVER

This application is a Continuation-In-Part of U.S. patent application Ser. No. 08/471,038, filed Jun. 6, 1995, now abandoned, which is hereby incorporated by reference in its entirety.

1. INTRODUCTION

The present invention relates to the Rasp-1 (regeneration-associated serpin-1) gene, a novel gene whose expression is up-regulated in regenerating liver tissue. The present invention further relates to the novel RASP-1 protein encoded by the Rasp-1 gene. In addition, the present invention relates to methods and compositions for the diagnosis and treatment of liver disease.

2. BACKGROUND OF THE INVENTION

The liver is the heaviest gland of the body, weighing about 1.4 kg (about 3 lb) in the average adult, and is the second largest organ after the skin. It is almost completely covered by peritoneum and completely covered by a dense irregular connective tissue layer lying beneath the peritoneum. The liver is divided into two principal lobes: a large right lobe and a smaller left lobe. The lobes are separated by the falciform ligament, which is a reflection of the parietal peritoneum. It extends from the undersurface of the diaphragm to the superior surface of the liver, between the two principal lobes of the liver. In the free border of the falciform ligament is the ligamentum teres (round ligament). It extends from the liver to the umbilicus. The ligamentum teres is a fibrous cord that is a remnant of the umbilical vein of the fetus.

The lobes of the liver consist of many functional units called lobules. Each lobule consists of specialized epithelial cells, called hepatocytes (i.e., parenchymal cells), arranged in irregular, branching, interconnected plates around a central vein. Rather than capillaries, the sinusoids, through which blood passes. The sinusoids are partly lined with phagocytes called stellate reticuloendothelial (Kupffer's) cells.

The liver's main function is to control the level of particular substances in the blood. For instance, the liver plays a major role in carbohydrate metabolism by removing glucose from the blood, under the influence of the hormone insulin, and storing it as glycogen. When the level of glucose in the blood falls, the hormone glucagon causes the liver to break down glycogen and release glucose into the blood. The liver also plays an important role in protein metabolism, primarily through deamination of amino acids, as well as the conversion of the resulting toxic ammonia into urea, which can be excreted by the kidneys. The liver also detoxifies many drugs and hormones. In addition, the liver participates in lipid metabolism by storing triglycerides, breaking down fatty acids, and synthesizing lipoproteins. The liver also secretes bile, which helps in the digestion of fats, cholesterol, phospholipids, and lipoproteins. In addition, the liver stores vitamins (A, $B_{12}$, D, E, and K) and minerals (iron and copper). Furthermore, the Kupffer's cells of the liver phagocytize worn-out red and white blood cells as well as some bacteria. Bilirubin, a breakdown product of heme, is excreted by the liver into the bile ducts where it passes into the intestinal tract.

There are many different causes of liver disorders. Hepatitis, an inflammation of the liver, is commonly caused by alcoholism or other toxic ingestion, or infection by viruses or other parasites. Cirrhosis of the liver is marked by the destruction of parenchymal cells and their replacement with connective tissue. Hepatitis resulting from infection by hepatitis C virus, for example, often develops into cirrhosis. Hepatitis B virus infection, on the other hand, is strongly believed to lead in many cases to liver cancer (hepatoma). Hepatoma can also be caused by the activation of endogenous oncogenes, through exposure to carcinogens, for example.

Severe forms of these disorders may result in chronic or acute hepatic failure. Fulminant hepatic failure (FHP) is associated with massive necrosis of hepatocytes and concomitant sudden severe impairment of hepatic metabolism. The clinical picture is usually dominated by symptoms of severe attrition of mental functions—a situation which, in most cases, rapidly advances to stupor or coma. An early onset of jaundice is also a characteristic finding and with increments of abnormal enzyme blood levels, these patients usually die within a week. Partial or total liver replacement is needed in case of transient or permanent failure of vital liver functions. Even with recent advances in supportive therapy, patients with FHP still exhibit a mortality rate in excess of 80%.

Unlike other internal organs, the liver has a remarkable capacity to regenerate. In the rat, for example, a 70% hepatectomized liver will regenerate its original mass in about seven days. Nonetheless, because the liver carries out so many important biochemical functions, severe liver damage or loss of the liver is rapidly fatal. Some efforts have been made, therefore, to identify the molecular factors involved in the liver regeneration process.

Most previous studies have focused on events occurring in the first few (e.g., 1–6) hours after surgery. In this regard, Hagiya et al., 1994, Proc. Natl. Acad. Sci. USA 9:8142–8146, cloned ALR (augmenter of liver regeneration) from rat; Hsu et al., 1992, Mol. Cell Biol. 12:4654–4665, identified a gene encoding a novel leucine-zipper containing protein termed liver regeneration factor-1 (LRF-1); and Mohn et al., 1991, Mol. Cell Biol. 11:381–390, identified 41 novel immediate-early partial DNA sequences. These genes were isolated by examining expression during early time periods following partial hepatectomy (e.g., 1–6 hr). During this early stage of regeneration, the expression of acute phase inflammatory proteins is substantially high, thereby yielding a "background" of induced expression of genes which are not very useful because their expression is not specific to liver regeneration. Overcoming this lack of specificity may be a determining factor in obtaining urgently needed tools for early diagnosis of liver disorders, as well as improvements in therapy that take advantage of the liver's unusual regenerative capacity.

3. SUMMARY OF THE INVENTION

The present invention relates to the novel Rasp-1 gene, whose expression is up-regulated during regeneration of liver tissue, and to nucleic acids derived from this gene. Unlike previously identified genes whose induced expression is limited to the early stages of liver regeneration, the induction of Rasp-1 expression is observed well into the later stages (48 hr. post surgery) of liver regeneration, after general acute phase inflammatory gene expression has subsided. DNA sequences corresponding to the Rasp-1 gene, and their derivatives, have a variety of uses in accordance with the invention, including, but not limited to, the production of RASP-1 protein and the control of expression of the Rasp-1 gene in liver tissue. The present invention also relates to the protein products encoded by the Rasp-1 gene, which may represent protein factors playing an important role in liver regeneration. The Rasp-1 gene product, RASP-1, is secreted into the blood stream. Such protein products can be used in the treatment of liver damage or disease, by stimulating, for example, the regeneration of intracorporeal liver tissue, or enhancing the growth of extracorporeal liver tissue. These protein products may also exert growth regulatory activity on other types of cells and tissues, including, but not limited to, fibroblasts and cartilage, as well as cells having hematopoietic potential. Additionally, the invention relates to antibodies against the Rasp-1 gene products. The antibodies can be used in the diagnosis of liver disease and damage, by detecting, for example, the presence of RASP-1 secreted into the bloodstream.

4. DESCRIPTION OF THE FIGURES

Figure 1A:
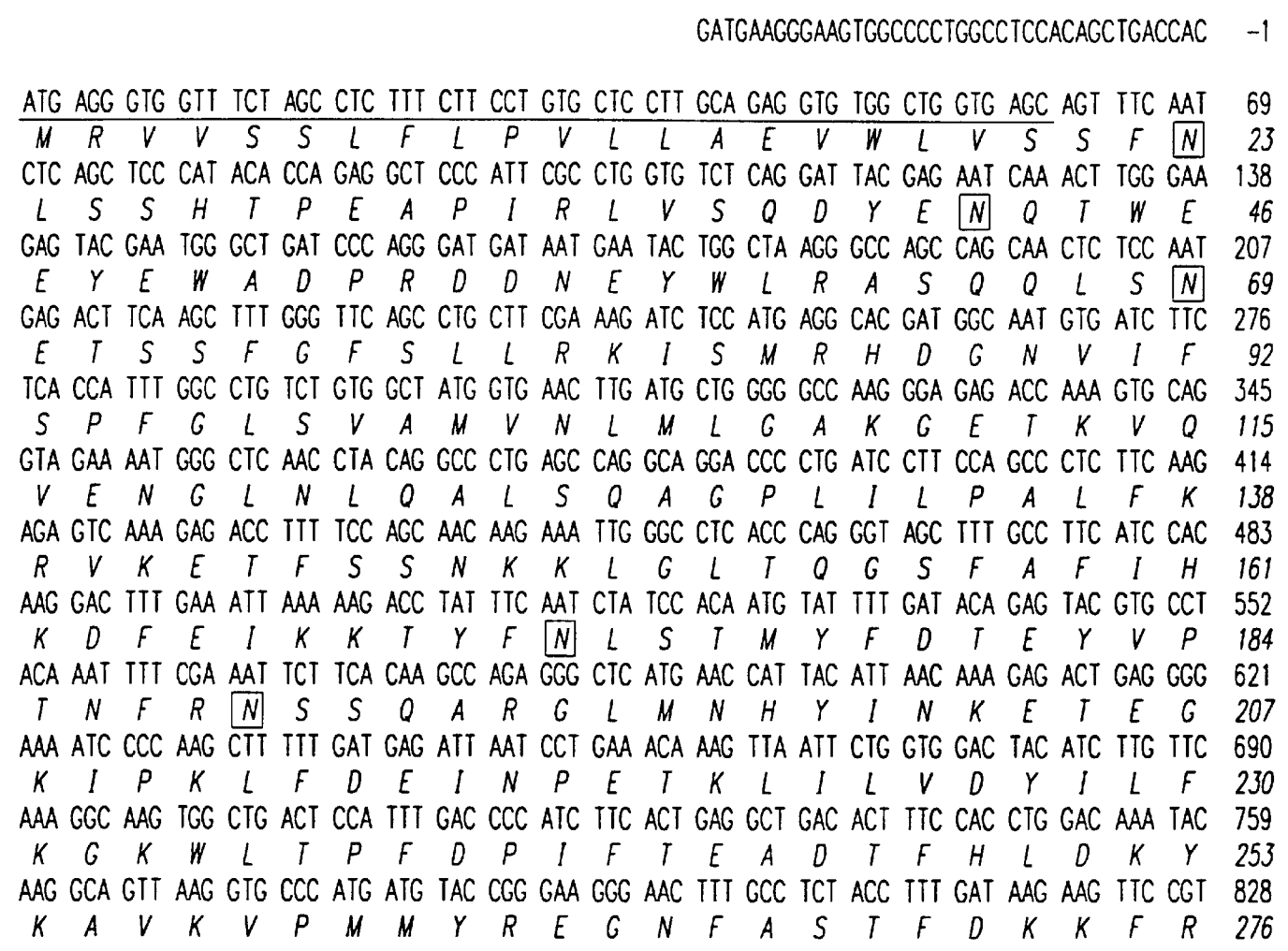
Figure 1B:
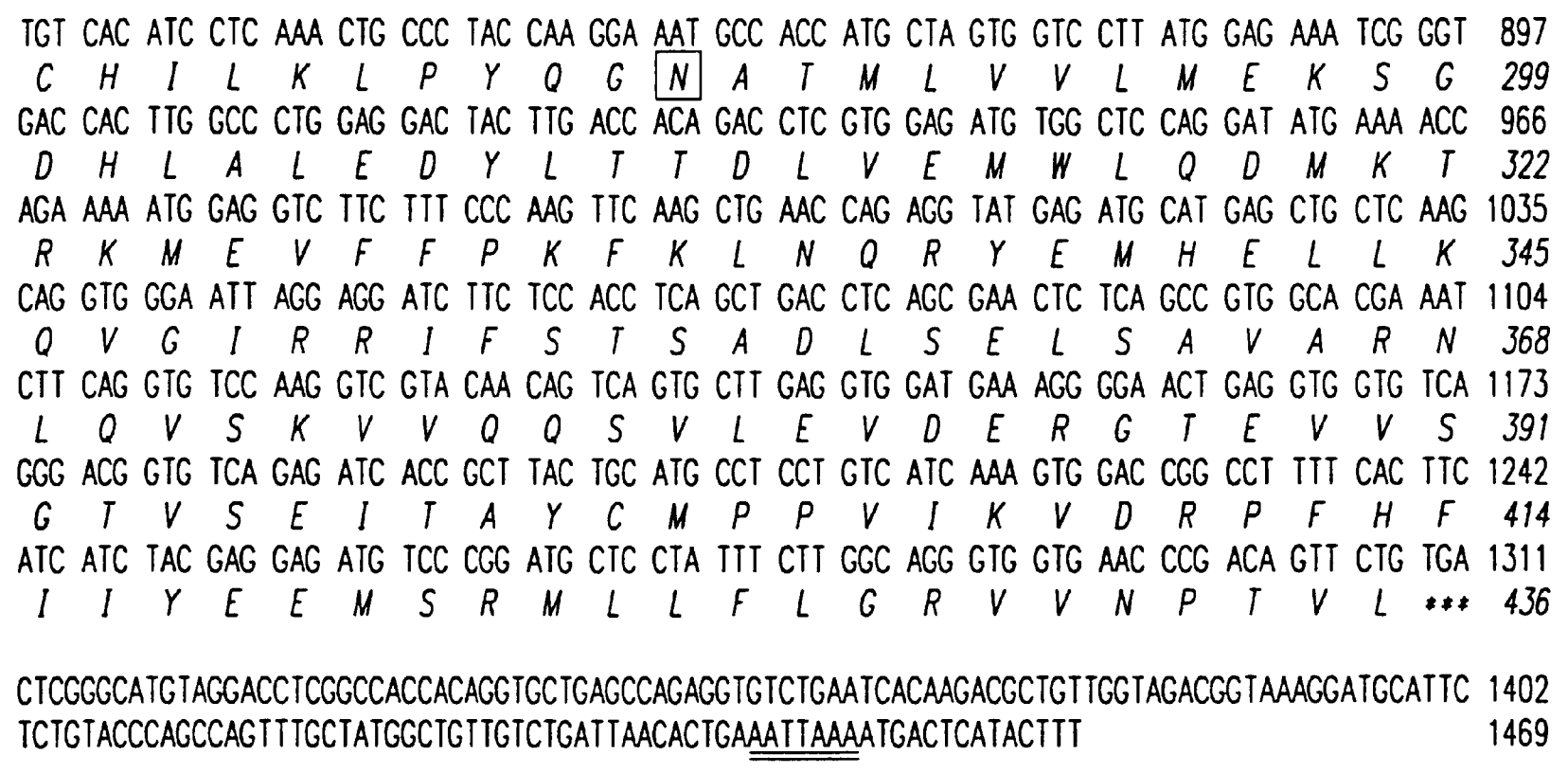

FIG. 1. DNA (SEQ ID NO:1) and encoded amino acid (SEQ ID NO:2) sequence of the novel Rasp-1 gene. The signal sequence is single underlined and the potential polyadenylation signal (AATTAAA) is double underlined. Five asparagine (N) residues for potential glycosylation are boxed as analyzed by GENEPRO 5™ (Riverside Scientific Enterprises).

FIG. 2. Northern blot analysis of Rasp-1 mRNA in normal (N) versus regenerating (R) liver tissue. 10 μg total liver RNA samples isolated from normal (N) and 48 hr. post hepatectomized animals were probed with a 1.6 kb Rasp-1 cDNA.

Figure 3A:
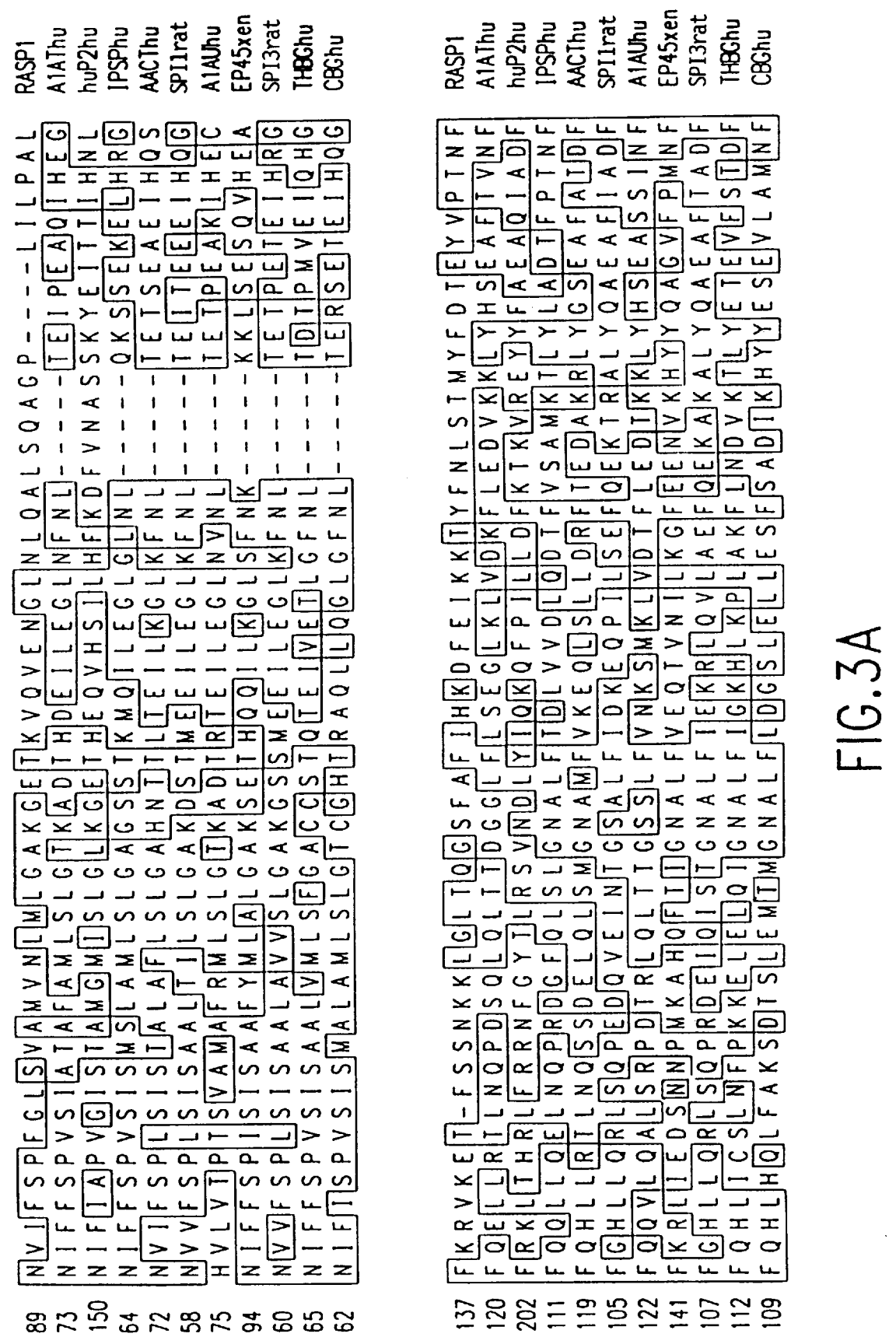
Figure 3B:
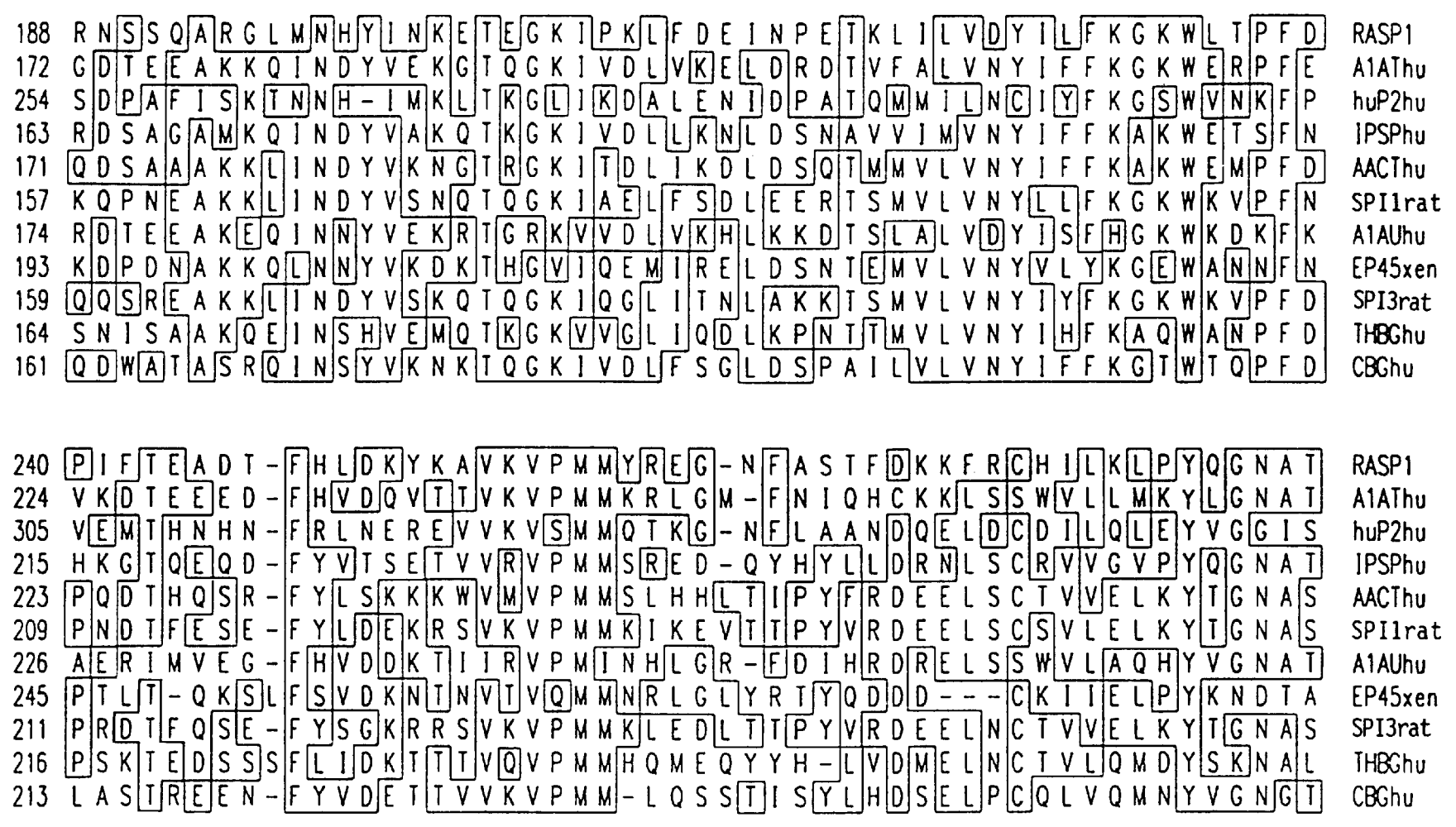
Figure 3C:
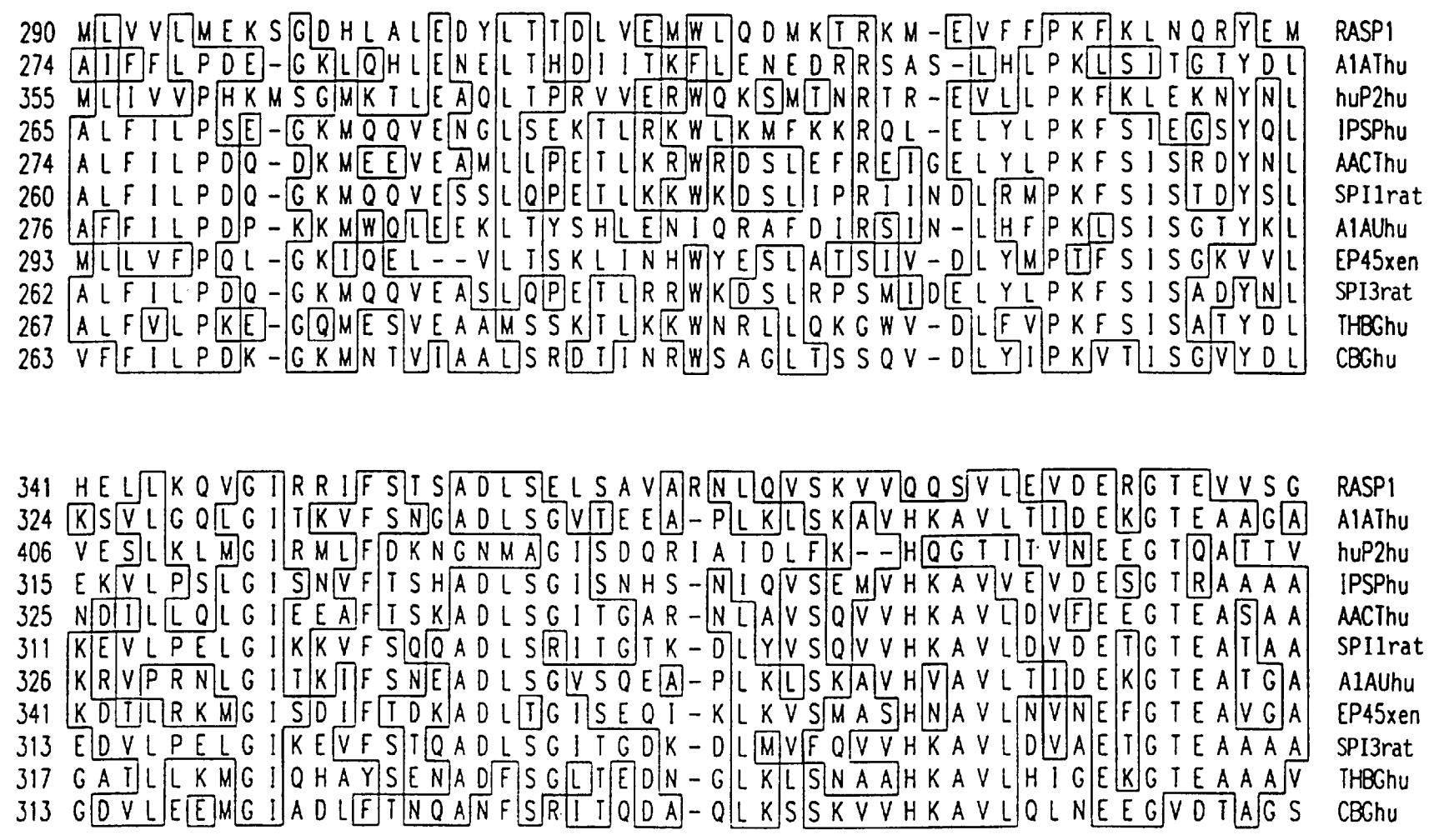
Figure 3D:
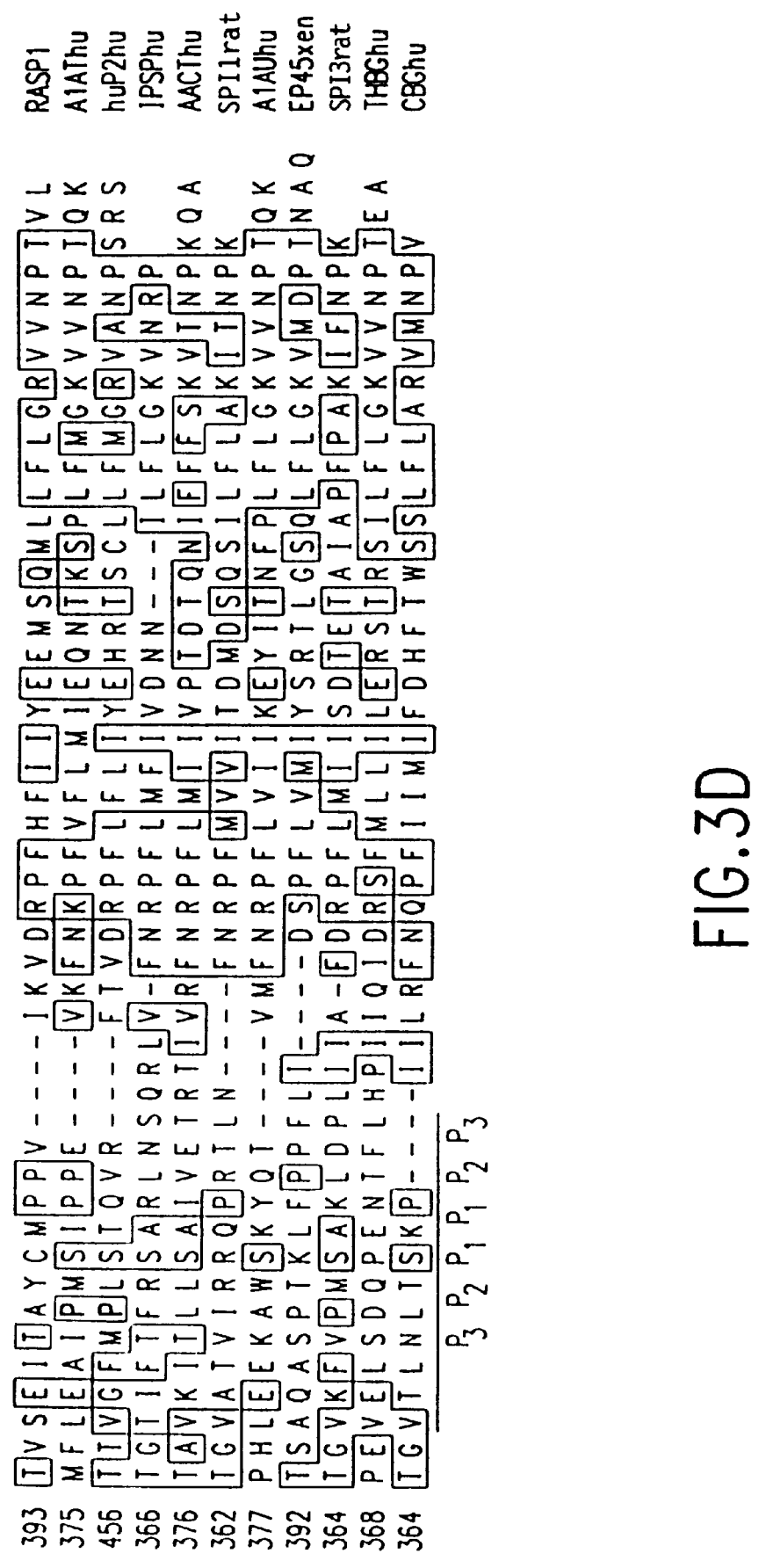

FIGS. 3A and 3B. FIG. 3A: Alignment of encoded RASP-1 amino acid sequence with homologous proteins. Alignment was performed using the Smith-Waterman algorithm of MPSRCH (IntelliGenetics). Homologous proteins are as follows: A1AT hu, human $\alpha_1$-antitrypsin precursor (Bollen et al, 1983, DNA 2:255–264); HEP2 hu, human heparin cofactor II precursor (Herzog et al., 1991, Biochemistry 30:1350–1357); IPSP hu, human plasminogen activator inhibitor-3 precursor (Suzuki et al., 1987, J. Biol. Chem. 262:611–616); AACT hu, human $\alpha_1$-antichymotrypsin precursor (Chandra et al., 1983, Biochem. 22: 5055–5061); SPI1 rat, rat serine protease inhibitor-1 precursor and SPI3 rat, rat serine protease inhibitor-3 precursor (Pages et al., 1990, Eur. J. Biochem 190:385–391); UAU-1 hu, human $\alpha_1$-antitrypsin related protein precursor (Bao et al., 1988, Genomics 2:165–173); EP45 Xen, Xenopus estrogen regulated protein EP45 (Holland et al., 1992, J. Biol. Chem. 267: 7053–7059); THBG hu, human thyroxine binding globulin precursor (Flink et al., 1986, Proc. Natl. Acad. Sci. USA 83: 7708–7712) and CBG hu, human corticosteroid-binding globulin precursor (Hammond et al., 1991, J. Steroid Biochem. Mol. Biol. 40: 755–762). The region around the putative serpin reactive center is underlined and the relative positions of residues flanking the assumed proteolytic cleavage bond between $P_1$-$P_1'$ are indicated. FIG. 3B: Table quantifying similarities and divergences among the eleven proteins in FIG. 3A. Overall homology was calculated from the pairwise alignment of the above homologous proteins by Clustal program with PAM250 residue weight metrics.

Figure 4:

FIG. 4. Western blot analysis of rat plasma from pre-immune serum (lane 1) versus serum after immunization with RASP-1 peptide (lane 2).

Figure 5:
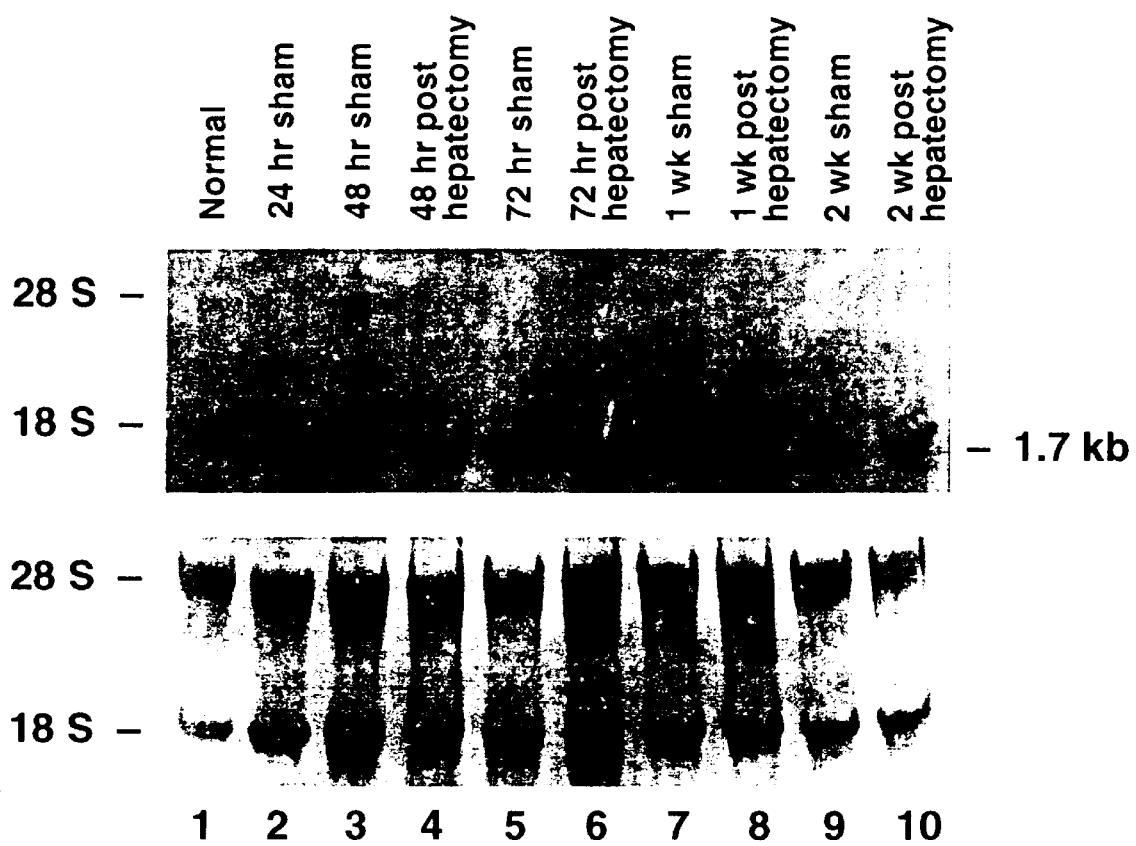

FIG. 5. Northern blot analysis of Rasp-1 expression following hepatectomy (HX) versus sham HX. Various μg RNA samples were loaded and probed with Rasp-1 cDNA. The Rasp-1 mRNA is indicated in the top panel. The bottom panel shows methylene blue stained total RNA on the same filter. The RNA sources were as follows: lane 1—Normal; lane 2—24 hr. post sham; lane 3—48 hr. post sham; lane 4—48 hr. post HX; lane 5—72 hr. post sham; lane 6—72 hr. post HX; lane 7—1 week post sham; lane 8—1 week post HX; lane 9—2 weeks post sham; lane 9—2 weeks post HX.

5. DETAILED DESCRIPTION OF THE INVENTION

The present invention relates to the identification of the novel Rasp-1 gene, whose expression is up-regulated in regenerating liver, RASP-1 proteins that are encoded by the Rasp-1 gene, and the use of the Rasp-1 gene and RASP-1 proteins in the regeneration of liver tissue and treatment of liver disease. The invention also relates to antibodies against RASP-1 proteins, and their use in diagnosing liver disorders and in monitoring liver regeneration.

5.1. The Rasp-1 Gene

The Rasp-1 gene is a novel gene, shown in FIG. 1, whose expression is up-regulated during the early stages of regeneration following hepatectomy. Nucleic acid sequences of the identified Rasp-1 gene are described herein. As used herein, "Rasp-1 gene" refers to (a) a gene containing the DNA sequence shown in FIG. 1 or contained in the clone pRLC-1 as deposited with the ATCC; (b) any DNA sequence that encodes the amino acid sequence shown in FIG. 1, or the amino acid sequence encoded by the clone pRLC-1 as deposited with the ATCC; (c) any DNA sequence that hybridizes to the complement of the coding sequences shown in FIG. 1 or contained in the clone pRLC-1 as deposited with the ATCC, under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., New York, at p. 2.10.3) and encodes a gene product functionally equivalent to a gene product encoded by sequences shown in FIG. 1 or contained within the clone pRLC-1; and/or (d) any DNA sequence that hybridizes to the complement of the coding sequences disclosed herein (as shown in FIG. 1), or contained in the clone pRLC-1 as deposited with the ATCC, under less stringent conditions, such as moderately stringent conditions, e.g., washing in 0.2×SSC/0.1% SDS at 42° C. (Ausubel et al., 1989, supra), and encodes a gene product functionally equivalent to a gene product encoded by sequences shown in FIG. 1 or contained within the clone pRLC-1.

The invention also includes nucleic acid molecules, preferably DNA molecules, that hybridize to, and are therefore the complements of, the DNA sequences (a) through (c), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as Rasp-1 gene antisense molecules, useful, for example, in Rasp-1 gene regulation and/or as antisense primers in amplification reactions of Rasp-1 gene nucleic acid sequences. Further, such sequences may be used as part of ribozyme and/or triple helix sequences, also useful for Rasp-1 gene regulation. Still further, such molecules may be used as components of diagnostic methods whereby the presence of a liver disease-causing allele may be detected.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include, but are not limited to, inducible and non-inducible promoters, enhancers, operators and other elements known to those skilled in the art that drive and regulate expression.

The invention includes fragments of any of the DNA sequences disclosed herein. Fragments of the Rasp-1 gene corresponding to coding regions of particular domains, or in which one or more of the coding regions of the domains is deleted (e.g., the sequence encoding the N-terminal signal peptide from amino acids 1–20 as shown in FIG. 1), are especially useful. Such Rasp-1 gene fragments may encode truncated gene products that are functionally equivalent to the full-length RASP-1 protein. Alternatively, such fragmented gene products may lack the activity corresponding to the deleted domain(s), or even entirely lack activity. The invention also includes mutant Rasp-1 genes encoding substitutions of amino acids as described below in Section 5.2, including but not limited to substitute residues at the N-linked glycosylation sites indicated by boxed asparagine residues (N) in FIG. 1.

In addition to the gene sequences described above, homologs of such sequences, as may, for example, be present in other species, including humans, may be identified and may be readily isolated, without undue experimentation, by molecular biological techniques well known in the art. Further, there may exist genes at other genetic loci within the genome that encode proteins which have extensive homology to one or more domains of such gene products. These genes may also be identified via similar techniques.

The Rasp-1 gene and its homologs can be obtained from a mammalian species, including but not limited to human, non-human primate, dog, cat, rat, mouse, hamster, etc. For obtaining cDNA, tissues and cells in which Rasp-1 is expressed are optimal. Tissues which can provide a source of genetic material for Rasp-1 and its homologs, therefore, include liver, including adult, embryonic, and fetal liver. Furthermore, specific cellular sources include especially liver derived cells, such as Hep G2, Hep 3B, PLC/PLF/5 (human), Hepa 1–6 (murine), and H4TG, McA-RH7777, and $MH_1C_1$ (rat).

For example, the isolated Rasp-1 gene sequence may be labeled and used to screen a cDNA library constructed from mRNA obtained from the organism of interest. The hybridization conditions used should be of a lower stringency when the cDNA library is derived from an organism different from the type of organism from which the labeled sequence was derived. Alternatively, the labeled fragment may be used to screen a genomic library derived from the organism of interest, again, using appropriately stringent conditions. Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Further, a previously unknown Rasp-1 gene-type sequence may be isolated by performing PCR using two degenerate oligonucleotide primer pools designed on the basis of amino acid sequences within the gene of interest. The template for the reaction may be cDNA obtained by reverse transcription of mRNA prepared from human or non-human cell lines or tissue known or suspected to express a Rasp-1 gene allele.

The PCR product may be subcloned and sequenced to ensure that the amplified sequences represent the sequences of a Rasp-1 gene-like nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to screen a genomic library.

PCR technology may also be utilized to isolate full length cDNA sequences. For example, RNA may be isolated, following standard procedures, from an appropriate cellular or tissue source. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

In cases where the Rasp-1 gene identified is the normal, or wild type, gene, this gene may be used to isolate mutant alleles of the gene. Mutant alleles may be isolated from individuals either known or proposed to have a genotype which contributes to liver disease symptoms. Mutant alleles and mutant allele products may then be utilized in the therapeutic and diagnostic systems described below.

A cDNA of the mutant gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from a tissue known to express or suspected of expressing the gene of interest in an individual suspected of or known to carry the mutant allele. The normal gene or any suitable fragment thereof may then be labeled and used as a probed to identify the corresponding mutant allele in the library. The clone containing this gene may then be purified and subjected to sequence analysis according to methods well known to those of skill in the art.

Additionally, an expression library can be constructed utilizing DNA isolated from or cDNA synthesized from liver tissue known to or suspected of expressing the gene of interest in an individual suspected of or known to carry the mutant allele. In this manner, gene products made by the putatively mutant tissue may be expressed and screened using standard antibody screening techniques in conjunction with antibodies raised against the normal gene product, as described, below, in Section 5.3. (For screening techniques, see, for example, Harlow, E. and Lane, eds., 1988, "Antibodies: A Laboratory Manual", Cold Spring Harbor Press, Cold Spring harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis according to methods well known to those of skill in the art.

5.2. Protein Products of the Rasp-1 Gene

The amino acid sequence encoded by the Rasp-1 gene is shown in FIG. 1. The Rasp-1 gene product may include those proteins encoded by the Rasp-1 gene sequences described in Section 5.1, above. Specifically, Rasp-1 gene products, sometimes referred to herein as "RASP-1 proteins", may include Rasp-1 gene product encoded by the Rasp-1 gene sequence shown in FIG. 1 or the gene sequence contained in the clone pRLC-1 as deposited with the ATCC, for example.

In addition, Rasp-1 gene products may include proteins that represent functionally equivalent gene products. Such an equivalent Rasp-1 gene product may contain deletions, additions or substitutions of amino acid residues within the amino acid sequence encoded by the Rasp-1 gene sequences described, above, in Section 5.1, but which result in a silent change, thus producing a functionally equivalent Rasp-1 gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous Rasp-1 gene products encoded by the Rasp-1 gene sequences described in Section 5.1, above, as judged by any of a number of criteria, including but not limited to antigenicity, i.e., the ability to bind to an anti-RASP-1 antibody, immunogenicity, i.e., the ability to generate an antibody which is capable of binding a RASP-1 protein or polypeptide; the ability to bind (or compete with RASP-1 for binding) to a substrate for RASP-1; the ability to bind RASP-1, the binding affinity for a RASP-1 receptor, the resulting biological effect of binding to a RASP-1 receptor, e.g., signal transduction, a change in cellular metabolism (e.g., ion flux, tyrosine phosphorylation) or change in phenotype when the RASP-1 equivalent is present in an appropriate cell type (such as the stimulation or inhibition of cellular growth and/or differentiation).

Included within the scope of the invention are RASP-1 proteins, polypeptides, and derivatives (including fragments) which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc. In a specific embodiment, the compositions of the invention are conjugated to other molecules to increase their water-solubility (e.g., polyethylene glycol), half-life, or ability to bind targeted tissue (e.g., biphosphonates and fluorochromes to target the proteins to bony sites).

Furthermore, nonclassical amino acids or chemical amino acid analogs can be introduced as a substitution or addition into the RASP-1 sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

While random mutations can be made to Rasp-1 DNA (using random mutagenesis techniques well known to those skilled in the art) and the resulting mutant RASP-1 proteins tested for activity, site-directed mutations of the Rasp-1 coding sequence can be engineered (using site-directed mutagenesis techniques well known to those skilled in the art) to generate mutant RASP-1 proteins with increased function, e.g., higher binding affinity for RASP-1 receptor and/or substrate; or decreased function, e.g., lower binding affinity for RASP-1 receptor and/or substrate.

For example, the alignment of RASP-1 and other serpins is shown in FIG. 3A, in which identical amino acid residues are indicated by a box. Mutant RASP-1 proteins can be engineered so that regions of identity (indicated by a box in FIG. 3A) are maintained, whereas the variable residues (outside of boxes in FIG. 3A) are altered, e.g., by deletion or insertion of an amino acid residue(s) or by substitution of one or more different amino acid residues. Conservative alterations at the variable positions can be engineered in order to produce a mutant RASP-1 that retains function; e.g., RASP-1 receptor or substrate binding affinity or both. Non-conservative changes can be engineered at these variable positions to alter function, e.g., RASP-1 binding affinity to receptor or substrate, or both. Alternatively, where alteration of function is desired, deletion or non-conservative alterations of the conserved regions (i.e., identical amino acids indicated by a box in FIG. 3A) can be engineered. For example, deletion or non-conservative alterations (substitutions or insertions) of the reactive center of RASP-1 (i.e., amino acids 395–405 of in FIG. 1, or in the top row of FIG. 3A) will alter enzymatic activity of RASP-1. Furthermore, alteration of the critical cysteine residue at amino acid 401 will lead to altered binding specificity of substrate.

Other mutations to the Rasp-1 coding sequence can be made to generate RASP-1 proteins that are better suited for expression, scale up, etc. in the host cells chosen. For example, N-linked glycosylation sites (indicated by boxed N residues in FIG. 1) can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur in the RASP-1 protein (N-X-S or N-X-T) will prevent glycosylation at the modified tripeptide sequence. See, e.g., Miyajima et al., 1986, EMBO J. 5(6):1193–1197.

Peptides corresponding to one or more domains of the RASP-1 (e.g., N-terminal signal peptide from amino acids 1–20 as shown in FIG. 1), truncated or deleted RASP-1 proteins (e.g., RASP-1 in which signal is deleted) as well as fusion proteins in which the full length RASP-1 protein, polypeptide or derivative (including fragment), or truncated RASP-1 (consisting of the signal sequence, or lacking the signal sequence), is fused to an unrelated protein are also within the scope of the invention and can be designed on the basis of the Rasp-1 nucleotide and RASP-1 amino acid sequences disclosed in this Section and in Section 5.1, above. The fusion protein may also be engineered to contain a cleavage site located between a RASP-1 sequence and the non-RASP-1 protein sequence, so that the RASP-1 protein may be cleaved away from the non-RASP-1 moiety. Such fusion proteins include but are not limited to IgFc fusions which stabilize the RASP-1 protein or peptide and prolong half-life in vivo; or fusions to an enzyme, fluorescent protein, or luminescent protein which provide a marker function.

The Rasp-1 gene products may be produced by recombinant DNA technology using techniques well known in the art. Thus, methods for preparing the Rasp-1 gene polypeptides and peptides of the invention by expressing nucleic acid containing Rasp-1 gene sequences are described herein. Methods which are well known to those skilled in the art can be used to construct expression vectors containing Rasp-1 gene product coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding Rasp-1 gene product sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety. The use of such a synthetic peptide fragment of RASP-1 for generating polyclonal antibodies is described in the example in Section 6, below.

A variety of host-expression vector systems may be utilized to express the Rasp-1 gene coding sequences of the invention. Such host-expression systems represent vehicles by which the coding sequences of interest may be produced and subsequently purified, but also represent cells which may, when transformed or transfected with the appropriate nucleotide coding sequences, exhibit the Rasp-1 gene product of the invention in situ. These include but are not limited to microorganisms such as bacteria (e.g., *E. coli, B. subtilis*) transformed with recombinant bacteriophage DNA, plasmid DNA or cosmid DNA expression vectors containing Rasp-1 gene product coding sequences; yeast (e.g. Saccharomyces, Pichia) transformed with recombinant yeast expression vectors containing the Rasp-1 gene product coding sequences; insect cell systems infected with recombinant virus expression vectors (e.g., baculovirus) containing the Rasp-1 gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing Rasp-1 gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the Rasp-1 gene product being expressed. For example, when a large quantity of such a protein is to be produced, for the generation of pharmaceutical compositions of RASP-1 protein or for raising antibodies to RASP-1 protein, for example, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the Rasp-1 gene product coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. PGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The Rasp-1 gene coding sequence may be cloned individually into non-essential regions (for example the polyhedrin gene) of the virus and placed under control of an AcNPV promoter (for example the polyhedrin promoter). Successful insertion of Rasp-1 gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the Rasp-1 gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing Rasp-1 gene product in infected hosts (e.g., See Logan & Shenk, 1984, Proc. Natl. Acad. Sci. USA 81:3655–3659). Specific initiation signals may also be required for efficient translation of inserted Rasp-1 gene product coding sequences. These signals include the ATG initiation codon and adjacent sequences. In cases where an entire Rasp-1 gene, including its own initiation codon and adjacent sequences, is inserted into the appropriate expression vector, no additional translational control signals may be needed. However, in cases where only a portion of the Rasp-1 gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153: 516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably express the Rasp-1 gene product may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Rasp-1 gene product. Such engineered cell lines may be particularly useful in screening and evaluation of compounds that affect the endogenous activity of the Rasp-1 gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

An alternative fusion protein system allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$·nitriloacetic acid-agarose columns and histidine-tagged proteins are selectively eluted with imidazole-containing buffers.

The Rasp-1 gene products can also be expressed in transgenic animals. Animals of any species, including, but not limited to, mice, rats, rabbits, guinea pigs, pigs, micropigs, goats, and non-human primates, e.g., baboons, monkeys, and chimpanzees may be used to generate Rasp-1 transgenic animals.

Any technique known in the art may be used to introduce the Rasp-1 gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the Rasp-1 gene transgene be integrated into the chromosomal site of the endogenous Rasp-1 gene, gene targeting is preferred. Briefly, when such a technique is to be utilized, vectors containing some nucleotide sequences homologous to the endogenous Rasp-1 gene are designed for the purpose of integrating, via homologous recombination with chromosomal sequences, into and disrupting the function of the nucleotide sequence of the endogenous Rasp-1 gene. The transgene may also be selectively introduced into a particular cell type, thus inactivating the endogenous Rasp-1 gene in only that cell type, by following, for example, the teaching of Gu et al. (Gu, et al., 1994, Science 265: 103–106). The regulatory sequences required for such a cell-type specific inactivation will depend upon the particular cell type of interest, and will be apparent to those of skill in the art.

Once transgenic animals have been generated, the expression of the recombinant Rasp-1 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of Rasp-1 gene-expressing tissue, may also be evaluated immunocytochemically using antibodies specific for the Rasp-1 transgene product.

5.3. Antibodies to Rasp-1 Proteins

Antibodies that define the Rasp-1 gene product are within the scope of this invention, and include antibodies capable of specifically recognizing one or more Rasp-1 gene product epitopes. Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a Rasp-1 gene product in a biological sample, including, but not limited to, blood plasma and serum. Alternatively, the antibodies may be used as a method for the inhibition of abnormal Rasp-1 gene product activity. Thus, such antibodies may be utilized as part of liver disease treatment methods, and/or may be used as part of diagnostic techniques whereby patients may be tested for abnormal levels of Rasp-1 gene products, or for the presence of abnormal forms of the such proteins. Furthermore, such antibodies may be utilized to monitor the expression of the Rasp-1 gene during the process of liver regeneration.

For the production of antibodies against a Rasp-1 gene product, various host animals may be immunized by injection with a Rasp-1 gene product, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a Rasp-1 gene product, or an antigenic functional derivative thereof. The generation of polyclonal antibodies against a synthetic RASP-1 peptide is described in the example in Section 6, below. In general, for the production of polyclonal antibodies, host animals such as those described above, may be immunized by injection with Rasp-1 gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against Rasp-1 gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

5.4. Methods for Diagnosing Liver Disorders

The antibodies described in Section 5.3, above, can be used in the diagnosis of liver disorders. Such disorders include, but are not limited to hepatitis, cirrhosis, hepatoma, and FHP. In such disorders, damage to the liver may result in the up-regulation of the expression of the genes described in Section 5.1, above. Consequently, an excess amount of RASP-1 protein may be produced as compared with normal liver. In addition, as in the case of hepatoma, excessive up-regulation of the Rasp-1 gene may also give rise to the liver disorder. To detect such disorders, an appropriate biological sample can be treated with labeled antibody against RASP-1 protein to determine the level of RASP-1 protein being produced. A liver disorder will be indicated by an excess amount of RASP-1 protein detected in comparison to that detected in the sample from a normal subject.

RASP-1 protein from blood or other tissue or cell type may easily be isolated using techniques which are well known to those of skill in the art. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, New York), which is incorporated herein by reference in its entirety.

Preferred diagnostic methods for the detection of wild type or mutant RASP-1 proteins may involve, for example, immunoassays wherein RASP-1 proteins are detected by their interaction with an anti-RASP-1 protein specific antibody.

For example, antibodies, or fragments of antibodies, such as those described, above, in Section 5.3, useful in the present invention may be used to quantitatively or qualitatively detect the presence of wild type or mutant RASP-1 proteins. This can be accomplished, for example, by immunofluorescence techniques employing a fluorescently labeled antibody (see below) coupled with light microscopic, flow cytometric, or fluorimetric detection. Such techniques are especially preferred if the RASP-1 proteins are expressed on the cell surface.

The antibodies (or fragments thereof) useful in the present invention may, additionally, be employed histologically, as in immunofluorescence or immunoelectron microscopy, for in situ detection of RASP-1 proteins. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the RASP-1 protein, but also its distribution in the examined tissue. Using the present invention, those of ordinary skill will readily perceive that any of a wide variety of histological methods (such as staining procedures) can be modified in order to achieve such in situ detection.

Immunoassays for wild type or mutant RASP-1 proteins typically comprise incubating a biological sample, such as a biological fluid, including but not limited to, blood plasma or blood serum, a tissue extract, freshly harvested cells, or cells which have been incubated in tissue culture, in the presence of a detectably labeled antibody capable of identifying RASP-1 proteins, and detecting the bound antibody by any of a number of techniques well known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled RASP-1 protein specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the is present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-wild type or mutant anti-RASP-1 protein antibody may be determined according to well known methods. Those skilled in the art will be able to determine operative and optimal assay conditions for each determination by employing routine experimentation.

One of the ways in which the RASP-1 protein specific antibody can be detectably labeled is by linking the same to an enzyme and use in an enzyme immunoassay (EIA) (Voller, "The Enzyme Linked Immunosorbent Assay (ELISA)", Diagnostic Horizons 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) Enzyme Immunoassay, CRC Press, Boca Raton, Fla., 1980; Ishikawa, et al., (eds.) Enzyme Immunoassay, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alphaglycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect wild type or mutant RASP-1 proteins through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.5. Methods for Treatment, Regeneration, and Growth of Liver Tissue by use of Rasp-1 Gene Products

5.5.1. Treatment of Intracorporeal Liver Tissue

The Rasp-1 gene products described in Section 5.2, above, may be used to enhance the growth or regeneration of liver tissue in a variety of situations. In some cases, a patient's liver may be damaged but not beyond repair. For example, and not by way of limitation, excessive consumption of alcohol often leads to cirrhosis of the liver. Hepatocyte destruction can be arrested by discontinuation of alcohol consumption, but recovery will be facilitated and may require subsequent regeneration of the liver. In such cases, the natural regeneration process may be impaired due to extensive liver damage. In any event, treatment of the patient with pharmaceutical compositions, as described below in Section 5.8, comprising a Rasp-1 gene product will enhance regeneration and thereby speed recovery.

In some situations, treatment may require transplanting all or a section of the liver of a donor. Regeneration of both a living donor's and a recipient's liver during such transplantation treatments will be aided by administering pharmaceutical compositions, as described below in Section 5.8, comprising a Rasp-1 gene product.

In other situations, an artificial liver, produced according to the methods described in Section 5.5.2, below, for example, may be implanted into a patient suffering from liver disease. It may be sufficient and desirable to implant such an artificial liver at a stage where it has not yet attained the biological capacity of a normal liver. To increase the capacity of such an implant, the growth rate can be enhanced by administering pharmaceutical compositions, as described below in Section 5.8, comprising a Rasp-1 gene product.

In cases where a patient's natural liver is damaged or diseased, it may be left intact or only partially removed, but still require support from implanted artificial liver tissue or liver tissue transplanted from a donor. Pharmaceutical compositions comprising a Rasp-1 gene product can be used also in such cases to enhance the growth of the patient's natural liver tissue, as well as the implanted or transplanted liver tissue.

The use of Rasp-1 gene product in enhancing cell growth may be applied to other tissues, as well, including, but not limited to, hematopoietic cells.

5.5.2. In Vitro Liver Tissue Cultures

In vitro liver tissue cultures have a variety of uses. In treating patients suffering from liver damage or disease, for example, the liver tissue cultures can be used to support or replace the natural liver, by direct implantation or as part of an extracorporeal liver device. In addition, such liver tissue cultures can serve as models for testing the toxicity of drugs and other compounds.

Functional in vitro liver tissue may be generated, for example, and not by way of limitation, using the three-dimensional tissue culture system described in U.S. Pat. No. 5,266,480, which is incorporated herein by reference in its entirety. According to this system, hepatocytes may be isolated by conventional methods (Berry and Friend, 1969, J. Cell Biol. 43:506–520) which can be adapted for human liver biopsy or autopsy material. Briefly, a canula is introduced into the portal vein or a portal branch and the liver is perfused with calcium-free or magnesium-free buffer until the tissue appears pale. The organ is then perfused with a proteolytic enzyme such a collagenase solution at an adequate flow rate. This should digest the connective tissue framework. The liver is then washed in buffer and the cells are dispersed. The cell suspension may be filtered through a 70 μm nylon mesh to remove debris. Hepatocytes may be selected from the cell suspension by two or three differential centrifugations.

For perfusion of individual lobes of excised human liver, HEPES buffer may be used. Perfusion of collagenase in HEPES buffer may be accomplished at the rate of about 30 ml/minute. A single cell suspension is obtained by further incubation with collagenase for 15–20 minutes at 37° C. (Guguen-Guillouzo and Guillouzo, eds., 1986, "Isolated and Culture Hepatocytes", Paris, INSERM, and London, John Libbey Eurotext, pp. 1–12; 1982, Cell Biol. Int. Rep. 6:625–628).

The isolated hepatocytes may then be used to inoculate the three dimensional stroma. The inoculated stroma can be cultured according to the teachings of U.S. Pat. No. 5,266,480, as described for bone marrow and skin, in order to replicate the hepatocytes in vitro, in a system comparable to physiologic conditions. In addition, the growth rate and development of the three-dimensional liver culture, or of liver tissue cultures grown by alternative methods, may be enhanced by adding Rasp-1 gene products to the growth medium. This should result in an increased functional expression by the hepatocytes.

5.6. Methods for Treatment of Liver Disease by Affecting Rasp-1 Gene Expression Described below are methods whereby liver disorders may be treated with the nucleic acid sequences described in Section 5.1, above. In certain cases, including but not limited to cirrhosis, an increase in Rasp-1 gene product activity would facilitate regeneration or amelioration of liver damage. Furthermore, certain liver diseases may be brought about, at least in part, by the absence or reduction of the level of Rasp-1 gene expression. As such, an increase in the level of gene expression would bring about the amelioration of liver disease symptoms. Techniques for increasing Rasp-1 gene expression levels are discussed in Section 5.6.1, below.

In some cases, including but not limited to hepatoma, liver diseases may be brought about, at least in part, by an excessive level of Rasp-1 gene product, or by the presence of a Rasp-1 gene product exhibiting an abnormal or excessive activity. As such, the reduction in the level and/or activity of such gene products would bring about the amelioration of liver disease symptoms. Techniques for the reduction of Rasp-1 gene expression levels are discussed in Section 5.6.2, below.

5.6.1. Methods for Restoring or Increasing Rasp-1 Gene Expression

The Rasp-1 gene may be underexpressed within liver disorder situations. Described in this section are methods whereby the level of Rasp-1 gene expression may be increased to levels wherein liver disease symptoms are ameliorated, or liver regeneration is enhanced, or both.

For example, RNA sequences encoding Rasp-1 gene product may be directly administered to a patient exhibiting liver disease symptoms, at a concentration sufficient to produce a level of Rasp-1 gene product such that liver disease symptoms are ameliorated. Any of the techniques discussed, below, in Section 5.8, which achieve intracellular administration of compounds, such as, for example, liposome administration, may be utilized for the administration of such RNA molecules. The RNA molecules may be produced, for example, by recombinant techniques such as those described, above, in Section 5.2.

Further, patients may be treated by gene replacement therapy. One or more copies of a normal Rasp-1 gene, or a portion of the gene that directs the production of a normal Rasp-1 gene product with Rasp-1 gene function, may be inserted into cells using vectors which include, but are not limited to adenovirus, adeno-associated virus, and retrovirus vectors, in addition to other particles that introduce DNA into cells, such as liposomes. Additionally, techniques such as those described above may be utilized for the introduction of normal Rasp-1 gene sequences into human cells. Expression of the RNA or DNA sequences may be optimized according to the recombinant methods described in Section 5.2, above.

Cells, preferably autologous cells, containing normal Rasp-1 gene expressing sequences may then be introduced or reintroduced into the patient at positions which allow for the amelioration of liver disease symptoms. Such cell replacement techniques may be preferred, for example, when the Rasp-1 gene product is to be a secreted, extracellular gene product.

5.6.2. Methods and Compounds for Inhibiting Expression of Rasp-1 Genes

As discussed above, abnormal Rasp-1 genes can cause liver disorders via an increased level of Rasp-1 gene product activity. A variety of techniques may be utilized to inhibit the expression of such Rasp-1 genes.

Among the compounds which may exhibit the ability to ameliorate liver disease symptoms are antisense, ribozyme, and triple helix molecules derived from the sequences described in Section 5.1, above. Such molecules may be designed to reduce the level of excessive or abnormal (e.g., mutant) Rasp-1 gene expression. Techniques for the production and use of such molecules are well known to those of skill in the art.

Anti-sense RNA and DNA molecules act to directly block the translation of mRNA by hybridizing to Rasp-1 mRNA and preventing protein translation. With respect to antisense DNA, oligodeoxyribonucleotides derived from the translation initiation site, e.g., between the −10 and +10 regions of the Rasp-1 gene nucleotide sequence are preferred.

Ribozymes are enzymatic RNA molecules capable of catalyzing the specific cleavage of RNA. The mechanism of ribozyme action involves sequence specific hybridization of the ribozyme molecule to complementary Rasp-1 RNA, followed by an endonucleolytic cleavage. The composition of ribozyme molecules must include one or more sequences complementary to the Rasp-1 gene mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding Rasp-1 gene products.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the Rasp-1 gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules to be used in triple helix formation for the inhibition of transcription should be single stranded and composed of deoxyribonucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

It is possible that the antisense, ribozyme, and/or triple helix molecules described herein may reduce or inhibit the transcription (triple helix) and/or translation (antisense, ribozyme) of mRNA produced by both normal and mutant Rasp-1 gene alleles. In order to ensure that substantially normal levels of Rasp-1 gene product activity are maintained, nucleic acid molecules that encode and express Rasp-1 gene polypeptides exhibiting normal activity may be introduced into cells that do not contain sequences susceptible to whatever antisense, ribozyme, or triple helix treatments are being utilized. Alternatively, it may be preferable to coadminister normal Rasp-1 gene product into the cell or tissue in order to maintain the requisite level of cellular or tissue Rasp-1 gene product activity.

Anti-sense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as, for example, solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

5.7. Methods for Treatment of Liver Disease by Inhibiting Rasp-1 Gene Product Activity As discussed above, liver disorders may be caused by excessive amounts and/or mutant forms of Rasp-1 gene product. Amelioration of such liver disorders may be brought about by inhibiting the activity of the harmful Rasp-1 gene product. A variety of techniques may be utilized to inhibit the activity of such Rasp-1 gene products.

Antibodies that are both specific for Rasp-1 gene product and interfere with its activity may be used to inhibit Rasp-1 gene product function. Such antibodies may be generated using standard techniques described in Section 5.3., supra, against the proteins themselves or against peptides corresponding to portions of the proteins. Such antibodies include but are not limited to polyclonal, monoclonal, Fab fragments, single chain antibodies, chimeric antibodies, etc.

In instances where the Rasp-1 gene product is intracellular and whole antibodies are used, internalizing antibodies may be preferred. However, lipofectin liposomes may be used to deliver the antibody or a fragment of the Fab region which binds to the Rasp-1 gene product epitope into cells. Where fragments of the antibody are used, the smallest inhibitory fragment which binds to the Rasp-1 gene product's binding domain is preferred. For example, peptides having an amino acid sequence corresponding to the domain of the variable region of the antibody that binds to the Rasp-1 gene product may be used. Such peptides may be synthesized chemically or produced via recombinant DNA technology using methods well known in the art (e.g., see Creighton, 1983, supra; and Sambrook et al., 1989, supra). Alternatively, single chain neutralizing antibodies which bind to intracellular Rasp-1 gene product epitopes may also be administered. Such single chain antibodies may be administered, for example, by expressing nucleotide sequences encoding single-chain antibodies within the target cell population by utilizing, for example, techniques such as those described in Marasco et al. (Marasco, W. et al., 1993, Proc. Natl. Acad. Sci. USA 90:7889–7893).

In instances where the Rasp-1 gene product is extracellular, or is a transmembrane protein, any of the administration techniques described, below, in Section 5.8, which are appropriate for peptide administration may be utilized to effectively administer inhibitory antibodies against Rasp-1 gene product to their site of action.

5.8. Pharmaceutical Preparations and Methods of Administration

The identified protein compounds that have liver regenerating activity or that affect Rasp-1 gene expression or gene product activity can be administered to a patient at therapeutically effective doses to treat or ameliorate liver disease. A therapeutically effective dose refers to that amount of the compound sufficient to result in amelioration of symptoms of liver disease.

5.8.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.8.2. Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

6. Identification of the Rasp-1 Gene

The identification of the novel gene, Rasp-1, is described herein. The Rasp-1 gene was identified based on its up-regulation in regenerating liver tissue (FIG. 2). The Rasp-1 gene encodes a RASP-1 protein which may play an important role in liver regeneration. cDNA sequence analysis indicates that RASP-1 is a secreted protein with a precursor of 436 amino acids (FIG. 1). The secretion of RASP-1 protein was confirmed by the detection of RASP-1 in the plasma of normal rats by a immunoblot (FIG. 4). In addition, Northern analysis of multiple rat tissues indicated that Rasp-1 was expressed only in liver and is probably a liver-specific gene. Both actual hepatectomy and sham hepatectomy stimulated Rasp-1 gene expression (FIG. 5). This result suggests that the signal leading to Rasp-1 transcription induced by surgical trauma for the acute phase response overlapped the signal for induction of transcription of Rasp-1 for the sequence-specific activation of genes controlling hepatic regeneration. Alternatively, Rasp-1 may have pleiotropic functions related to different microenvironment conditions. A homologous protein sequence alignment (FIG. 3) indicates that RASP-I belongs to the serine protease inhibitor superfamily. Thus, RASP-1 may be a novel proteinase inhibitor, and may, therefore, play a role in liver regeneration by preventing proteolytic degradation of extracellular stromal material during the regeneration process. Alternatively, RASP-1 may contribute to liver regeneration by inhibiting proteolysis of regulatory proteins thereby stimulating the mitogenic machinery of the parenchymal liver cells.

6.1. Materials and Methods

Hepatectomy:

A 70–90% hepatectomy was performed as previously described (Naughton et al., 1977, Science 196:301–302). Briefly, after the induction of metaphane anesthesia, the right and median hepatic lobes 6 wk old Long-Evans male rats were exteriorized through a ventromedian incision and ligated at the confluence of the right and medium hepatic veins and the inferior vena cava. The left lobe was extirpated in a similar manner so that 10–30% of the residual liver mass remained (Naughton el al., 1977, Science 196:301–302). Liver tissue excised during hepatectomy was used for normal controls. Sham operations were performed in an identical manner except that no liver tissue was extirpated. RNA extracted from the livers of two animals was pooled prior to analysis for each experimental group. Experiments were repeated 4 times.

RNA Extraction and Northern hybridization Analysis

Total RNA was extracted in guanidine thiocyanate solution as described by Chomczynski et al (I 987). The poly (A+) containing fraction was obtained by passing isolated total RNA through an oligo(dT)-cellulose column (Stratagene, La Jolla, Calif.). For Northern blots, 10 to 15 $\mu$g of total RNA was fractionated on a vertical 1% agarose gel containing 6% w/v formaldehyde and transferred on to a nylon membrane (Hybond N, Amersham) by capillary in 20x SSC buffer overnight followed by UV-crosslinking. Prehybridization and hybridization were carried out at 42° C. in a solution of 50% formamide, 5x SSPE buffer, 2xDenhardts' reagent and 0.2% sodium dodecyl sulfate (SDS) with yeast tRNA at a concentration of 0.8 mg/ml. 25 ng of cDNA synthesized from normal liver mRNA or regenerating liver mRNA or 0.5 $\mu$g of DNA fragment purified from agarose gel were $^{32}$P labeled using the Primer-It II random niner labeling kit (Stratagene, La Jolla, Calif.). After hybridization, blots were washed in 0.1% SDS and 0.2x SSC at 65° C. Before exposure, filters were stained in a solution containing 0.5M sodium acetate (pH 4.8) and 0.05% methylene blue to ensure equal loading and transfer of RNA.

Construction and Screening of cDNA Library

A cDNA library was constructed in λ-uniZAP (Stratagene, La Jolla, Calif.). Briefly, 5 $\mu$g of regenerating liver poly(A$^+$) RNA was reverse transcribed by M-MuL Reverse Transcriptase and DNA polymerase I was used for synthesis of second strand cDNAs. The cDNA termini were blunted by Klenow fragment and EcoRI adapters were ligated onto cDNAs. The cDNA fragments with the EcoRI site at the 5' end and the XhoI site at the 3' end were directionally ligated to predigested λ-uniZAP and packaged in Gigapack Gold λ packaging extracts (Stratagene, La Jolla, Calif.). The entire library was amplified by plating on E. coli strain XL1-Blue MRF'. A total of 1.5×10$^5$ library phages were plated and quadruplicated nitrocellulose membrane lifts for each plate were differentially screened with [$^{32}$P]-labeled cDNA probes made from normal and regenerating liver mRNAs by hybridizing two of the four lifts to a different probe, respectively. The primary positive plaques showing increased hybridization to the regenerating probe were selected for a second round differential screening by polymerase chain reaction (PCR) as described by Thomas, 1994, BioTechniques 16:229–231. The cDNA in the second round positive phages were excised out of the phage in a Bluescript plasmid by following the phagemid excision procedure (Stratagene, La Jolla, Calif.).

Analysis of cDNA Sequences and Predicted Amino Acid Sequence

A total of 36 positive isolates were purified and subjected to double strand nucleotide sequencing with T7 and T-3 primers flanking the inserts in Bluescript. Nucleotide sequences of ~200 bp were obtained from each end of the inserts. These nucleotide sequences and some of the deduced putative in-frame amino acid sequences were searched by Blast program (NCBI) to ascertain their homology and uniqueness (Altschul et al, 1990, J. Mol. Biol. 215:403–410). Most of the isolates were found to contain sequences completely identical to known genes in the Gen-Bank (Bilofsky and Burks, 1988, Nucl. Acids Res. 16:1861–1864) and some had mutually overlapping sequences. One clone, designated rlc11.3, contained a unique sequence. It did not contain a complete open reading frame, and included an unusual CT repeat at the 5' end. An approximately 300 bp fragment downstream of this CT repeat was used to probe the regenerating liver cDNA library. One positive clone, pRLC-1, was sequenced and found to contain a complete open reading frame which overlapped that of rlc11.3. Moreover, the 5' end of the complete open reading frame contained in pRLC-1 did not include the unusual CT repeat of rlc11.3. After further sequence analysis, the gene corresponding to the open reading frame contained in pRLC-1 was named Rasp-1 and chosen for further study.

pRLC-1 was deposited with the ATCC on Jun. 5, 1996, and assigned ATCC accession number 97603.

Antibody Generation and Immunoblotting

A peptide corresponding to the amino acid sequence encoded by the Rasp-1 gene, consisting of FKRVKETF-SSNKKLG (amino acids 137–151, see FIG. 1), was synthesized using a peptide synthesizer, conjugated to KLH, and injected into rabbits to evoke antibody formation. Preimmune blood serum was obtained and rabbits were injected intramuscularly with the peptide preparation twice during the first week. Serum was prepared from blood collected at two week intervals thereafter for up to 8 weeks. Rabbits were "boosted" at week 4. Western blot was performed as described by Burnette, 1981, A. Anal. Biochem., 112:195–203. Briefly, about 30 μg of rat plasma protein were electrophoresed on 8% SDS polyacrylamide gel and electrophoretically transferred onto a nitrocellulose membrane. Blots were blocked for 1 hr with 5% Carnation non-fat dry milk (Blotto) made in TBST (50 mM Tris, 500 mM NaCl, 0.05% tween 20, pH 7.5). The rabbit anti-sera were diluted to 1:100 in Blotto and incubated on the blot for 2 hr at 22° C. or 18 hr at 4° C. Alkaline phosphatase-conjugated goat anti-rabbit antibody (1:100 dilution in Blotto) was incubated with blots for 1 hr at 22° C. followed by incubation of the blots with substrates for alkaline phosphatase to disclose immunoreactive proteins.

6.2. Results

Identification of cDNAs Induced in Regenerating Liver

Thirty-six positive clones were isolated by differential screening of a regenerating liver cDNA library. Approximately 200 bp of cDNA from each end of the clones were sequenced. The sequence of clone pRLC-1, encoding a complete open reading frame, was found to be novel by Blast search. Completely sequencing the 1.6-kb insert of pRLC-1 identified a 1308-bp open reading frame encoding a deduced protein with 436 amino acids (FIG. 1). The first 20 amino acids residues at its amino terminus consisted of a typical hydrophobic secretory signal. Five potential N-glycosylation sites on the product of this gene are indicated in FIG. 1 by a boxed N. Because of the similarity of the encoded amino acid sequence to the serpin superfamily (FIGS. 3A and 3B), the novel gene contained in pRLC-1 was named Rasp-1 (Regeneration Associated Serpin 1).

Northern blot analysis of mRNA in normal animals and rats with regenerating livers show that the 1.7-kb Rasp-1 signal detected by the probe for this gene increased 4-fold by 48 hr. after subtotal hepatectomy over that of normal liver, indicating an association of RASP-1 with hepatic regeneration (FIG. 2).

When rat genomic DNA was digested by different restriction endonucleases (EcoRI, PstI and BamHI) and probed with a 300-bp fragment corresponding to the 5' coding region of Rasp-1, only single bands of different sizes were detected in each lane of the Southern blot (data not shown), indicating that there is a single copy of Rasp-1 in the rat genome.

RASP-1 is a Member in the Serpin Superfamily

FIG. 3A shows a multiple sequence alignment comparing part of RASP-1 (residues 89–436) with the first ten proteins having highest scores based upon overall similarity in Gen-Bank. All ten proteins are members of the serpin superfamily. Serpins are small glycoproteins (MWt 40–60 kD) with a single polypeptide chain glycosylated at a variable number of sites. They are highly recognizable by their structure homology presumably derived from an common ancestral serine proteinase inhibitor (Carrell and Boswell, 1986, Serpins: The Superfamily of Plasma Serine Proteinase Inhibitors in Proteinase Inhibitors; (Barrett, A. and Salvensen, G., Eds.), Elsevier, Amsterdam, pp. 403–420). Although the sequence of RASP-1 toward its amino terminus displayed less homology to these proteins, a highly homologous region was found on the carboxyl terminus that includes the conserved structure of reactive center for serpins (Carrell and Boswell, 1986, supra). Moderate similarities have also been observed through some other regions; FIG. 3B lists the overall homology scores of RASP-1 to each of these proteins.

A comparison of the reactive centers of these proteins to RASP-1 revealed that most serpins conserved a typical serine residue at the $P_1'$ site (Moiri and Travis, 1983, J. Biol. Chem. 258:12749–12752), whereas RASP-1 has a cystine at this position. This structure was unique compared not only to the proteins in the alignment but to other known serpins as well. The amino acid residues in the reactive centers, especially around the $P_1$ and $P_1'$ positions, were found to be important in defining reaction specificity (Carrell and Travis, 1985, Trends in Biochem. Sci. 10:20–24); Owen et al., 1983, N. Engl. J. Med. 309:694–698). The variations in reactive centers seen in FIG. 3A indicate a potentially diversified substrate interaction or binding specificity associated with each of these proteins.

Rasp-1 is expressed in liver tissue.

Northern blot analysis of total RNA isolated from different organs showed that Rasp-1 mRNA was strongly detected in normal liver but was not found in heart, lung, brain, spleen, testis, or kidney. This result indicates that liver is a predominant constitutive source of Rasp-1 gene product in normal subjects.

RASP-1 is a plasma protein

To identify the protein product of Rasp-1, a deduced peptide fragment (FKRVKETFSSNKKLG SEQ ID NO:3) of RASP-1 was used to generate polyclonal antibodies. Western analysis showed that the immune serum against this peptide identified a protein of the expected molecular weight (50 kD) in rat plasma (FIG. 4, lane 2). No protein was detected when preimmune serum was applied to the Western blot (FIG. 5, lane 1).

Effect of hepatectomy and sham hepatectomy on the regulation of Rasp-1 transcript To clarify the stimulatory signals associated with liver regeneration for the up-regulation of Rasp-1 transcripts, parallel operations were performed. Northern analysis revealed that Rasp-1 expression in liver was upregulated following subtotal hepatectomy and sham hepatectomy (FIG. 5). The hybridization signal at 24 hr after sham hepatectomy was ~8-fold higher than that observed in normal liver but it decreased by 48 hr after surgery and fluctuated thereafter, returning to near normal expression levels by 2 wk. Rasp-1 analysis of regenerating livers showed maximal expression of 3–4 X normal at 48 hr following subtotal hepatectomy with expression remaining elevated for up to 2 wk after liver removal.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims. All references cited herein are hereby incorporated, by reference, in their entireties.

What is claimed is:

1. An isolated nucleic acid which encodes a mammalian RASP-1 protein, said nucleic acid comprising a nucleotide sequence that:
   (a) encodes a polypeptide according to SEQ ID NO:2; or
   (b) encodes a polypeptide encoded by clone pRLC-1 as deposited with the ATCC and having ATCC Accession No. 97603.

2. An isolated nucleic acid comprising a nucleotide sequence encoding a mammalian RASP-1 N-terminal signal peptide corresponding to amino acids 1–20 of SEQ ID NO:2 or a truncated mammalian Rasp-1 polypeptide corresponding to amino acids 21–436 of SEQ ID NO:2.

3. An isolated nucleic acid comprising the coding region of SEQ ID NO:1.

4. An isolated nucleic acid which hybridizes under moderately stringent conditions of 42° C. in 0.2x SSC and 0.1% SDS to an mRNA encoding a mammalian RASP-1 protein that is expressed and upregulated in regenerating mammalian liver, and to either of:
   (a) the complement of the coding region of SEQ ID NO: 1; or
   (b) the complement of the coding region of clone pRLC-1 as deposited with the ATCC and having ATCC Accession No. 97603.

5. An isolated nucleic acid which is the complement of the isolated nucleic acid of claim 4.

6. An isolated nucleic acid which hybridizes under highly stringent conditions of 65° C. in 0.2x SSC and 0.1% SDS to either of:
   (a) an mRNA encoding a mammalian RASP-1 protein that is expressed and upregulated in regenerating mammalian liver;
   (b) the complement of the coding region of SEQ ID NO: 1; or
   (c) the complement of the coding region of clone pRLC-1 as deposited with the ATCC and having ATCC Accession No. 97603.

7. An isolated nucleic acid which is the complement of the isolated nucleic acid of claim 6.

8. A nucleotide vector comprising the nucleic acid of claim 1, 2, 3, 4, 5, 6, or 7.

9. An expression vector comprising the nucleic acid of claim 1, 2, 3, 4, 5, 6, or 7 in operative association with a nucleotide regulatory element that controls transcription of said nucleotide sequence.

10. An isolated genetically engineered host cell comprising the nucleic acid of claim 1, 2, 3, 4, 5, 6, or 7.

11. An isolated genetically engineered host cell comprising the nucleic acid of claim 1, 2, 3, 4, 5, 6, or 7, wherein said nucleic acid is in operative association with a nucleotide regulatory element that controls transcription of said nucleotide sequence in the host cell.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 1508 base pairs
      (B) TYPE: nucleic acid
      (C) STRANDEDNESS: single
      (D) TOPOLOGY: linear (xi) SEQUENCE DESCRIPTION: SEQ ID NO:1:

```
GATGAAGGGA AGTGGCCCCT GGCCTCCACA GCTGACCACA TGAGGGTGGT TTCTAGCCTC      60

TTTCTTCCTG TGCTCCTTGC AGAGGTGTGG CTGGTGAGCA GTTTCAATCT CAGCTCCCAT     120

ACACCAGAGG CTCCCATTCG CCTGGTGTCT CAGGATTACG AGAATCAAAC TTGGGAAGAG     180

TACGAATGGG CTGATCCCAG GGATGATAAT GAATACTGGC TAAGGGCCAG CCAGCAACTC     240

TCCAATGAGA CTTCAAGCTT TGGGTTCAGC CTGCTTCGAA AGATCTCCAT GAGGCACGAT     300

GGCAATGTGA TCTTCTCACC ATTTGGCCTG TCTGTGGCTA TGGTGAACTT GATGCTGGGG     360

GCCAAGGGAG AGACCAAAGT GCAGGTAGAA AATGGGCTCA ACCTACAGGC CCTGAGCCAG     420

GCAGGACCCC TGATCCTTCC AGCCCTCTTC AAGAGAGTCA AAGAGACCTT TTCCAGCAAC     480

AAGAAATTGG GCCTCACCCA GGGTAGCTTT GCCTTCATCC ACAAGGACTT TGAAATTAAA     540

AAGACCTATT TCAATCTATC CACAATGTAT TTTGATACAG AGTACGTGCC TACAAATTTT     600

CGAAATTCTT CACAAGCCAG AGGGCTCATG AACCATTACA TTAACAAAGA GACTGAGGGG     660

AAAATCCCCA AGCTTTTTGA TGAGATTAAT CCTGAAACAA AGTTAATTCT GGTGGACTAC     720

ATCTTGTTCA AAGGCAAGTG GCTGACTCCA TTTGACCCCA TCTTCACTGA GGCTGACACT     780

TTCCACCTGG ACAAATACAA GGCAGTTAAG GTGCCCATGA TGTACCGGGA AGGGAACTTT     840

GCCTCTACCT TTGATAAGAA GTTCCGTTGT CACATCCTCA AACTGCCCTA CCAAGGAAAT     900

GCCACCATGC TAGTGGTCCT TATGGAGAAA TCGGGTGACC ACTTGGCCCT GGAGGACTAC     960

TTGACCACAG ACCTCGTGGA GATGTGGCTC CAGGATATGA AAACCAGAAA AATGGAGGTC    1020

TTCTTTCCCA AGTTCAAGCT GAACCAGAGG TATGAGATGC ATGAGCTGCT CAAGCAGGTG    1080

GGAATTAGGA GGATCTTCTC CACCTCAGCT GACCTCAGCG AACTCTCAGC CGTGGCACGA    1140

AATCTTCAGG TGTCCAAGGT CGTACAACAG TCAGTGCTTG AGGTGGATGA AAGGGGAACT    1200

GAGGTGGTGT CAGGGACGGT GTCAGAGATC ACCGCTTACT GCATGCCTCC TGTCATCAAA    1260
```

```
GTGGACCGGC CTTTTCACTT CATCATCTAC GAGGAGATGT CCCGGATGCT CCTATTTCTT    1320

GGCAGGGTGG TGAACCCGAC AGTTCTGTGA CTCGGGCATG TAGGACCTCG GCCACCACAG    1380

GTGCTGAGCC AGAGGTGTCT GAATCACAAG ACGCTGTTGG TAGACGGTAA AGGATGCATT    1440

CTCTGTACCC AGCCAGTTTG CTATGGCTGT TGTCTGATTA ACACTGAAAT TAAAATGACT    1500

CATACTTT                                                            1508
```

(2) INFORMATION FOR SEQ ID NO:2:

(i) SEQUENCE CHARACTERISTICS:
        (A) LENGTH: 436 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:2:

```
Met Arg Val Val Ser Ser Leu Phe Leu Pro Val Leu Ala Glu Val
 1               5                  10                  15

Trp Leu Val Ser Ser Phe Asn Leu Ser Ser His Thr Pro Glu Ala Pro
                20                  25                  30

Ile Arg Leu Val Ser Gln Asp Tyr Glu Asn Gln Thr Trp Glu Glu Tyr
            35                  40                  45

Glu Trp Ala Asp Pro Arg Asp Asp Asn Glu Tyr Trp Leu Arg Ala Ser
    50                  55                  60

Gln Gln Leu Ser Asn Glu Thr Ser Ser Phe Gly Phe Ser Leu Leu Arg
65                  70                  75                  80

Lys Ile Ser Met Arg His Asp Gly Asn Val Ile Phe Ser Pro Phe Gly
                85                  90                  95

Leu Ser Val Ala Met Val Asn Leu Met Leu Gly Ala Lys Gly Glu Thr
            100                 105                 110

Lys Val Gln Val Glu Asn Gly Leu Asn Leu Gln Ala Leu Ser Gln Ala
        115                 120                 125

Gly Pro Leu Ile Leu Pro Ala Leu Phe Lys Arg Val Lys Glu Thr Phe
    130                 135                 140

Ser Ser Asn Lys Lys Leu Gly Leu Thr Gln Gly Ser Phe Ala Phe Ile
145                 150                 155                 160

His Lys Asp Phe Glu Ile Lys Lys Thr Tyr Phe Asn Leu Ser Thr Met
                165                 170                 175

Tyr Phe Asp Thr Glu Tyr Val Pro Thr Asn Phe Arg Asn Ser Ser Gln
            180                 185                 190

Ala Arg Gly Leu Met Asn His Tyr Ile Asn Lys Glu Thr Glu Gly Lys
        195                 200                 205

Ile Pro Lys Leu Phe Asp Glu Ile Asn Pro Glu Thr Lys Leu Ile Leu
    210                 215                 220

Val Asp Tyr Ile Leu Phe Lys Gly Lys Trp Leu Thr Pro Phe Asp Pro
225                 230                 235                 240

Ile Phe Thr Glu Ala Asp Thr Phe His Leu Asp Lys Tyr Lys Ala Val
                245                 250                 255

Lys Val Pro Met Met Tyr Arg Glu Gly Asn Phe Ala Ser Thr Phe Asp
            260                 265                 270

Lys Lys Phe Arg Cys His Ile Leu Lys Leu Pro Tyr Gln Gly Asn Ala
        275                 280                 285

Thr Met Leu Val Val Leu Met Glu Lys Ser Gly Asp His Leu Ala Leu
```

```
                    290                 295                 300
Glu Asp Tyr Leu Thr Thr Asp Leu Val Glu Met Trp Leu Gln Asp Met
305                 310                 315                 320

Lys Thr Arg Lys Met Glu Val Phe Phe Pro Lys Phe Lys Leu Asn Gln
                325                 330                 335

Arg Tyr Glu Met His Glu Leu Leu Lys Gln Val Gly Ile Arg Arg Ile
                340                 345                 350

Phe Ser Thr Ser Ala Asp Leu Ser Glu Leu Ser Ala Val Ala Arg Asn
                355                 360                 365

Leu Gln Val Ser Lys Val Val Gln Gln Ser Val Leu Glu Val Asp Glu
        370                 375                 380

Arg Gly Thr Glu Val Val Ser Gly Thr Val Ser Glu Ile Thr Ala Tyr
385                 390                 395                 400

Cys Met Pro Pro Val Ile Lys Val Asp Arg Pro Phe His Phe Ile Ile
                405                 410                 415

Tyr Glu Glu Met Ser Arg Met Leu Leu Phe Leu Gly Arg Val Val Asn
                420                 425                 430

Pro Thr Val Leu
        435

(2) INFORMATION FOR SEQ ID NO:3:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:3:

Phe Lys Arg Val Lys Glu Thr Phe Ser Ser Asn Lys Lys Leu Gly
1               5                   10                  15
```